United States Patent
Hefner, Jr. et al.

(10) Patent No.: US 12,071,394 B2
(45) Date of Patent: Aug. 27, 2024

(54) METHOD FOR REMOVING MONOISOCYANATES FROM ORGANIC SOLUTION

(71) Applicants: Dow Global Technologies LLC, Midland, MI (US); Dow Portugal Produtos Quimicos, Sociedade Unipessoal, LDA, Estarreja (PT)

(72) Inventors: Robert E. Hefner, Jr., Rosharon, TX (US); Helge Braun, Lake Jackson, TX (US); Armenio Costa, Estarreja (PT); Brian Cramm, Lake Jackson, TX (US)

(73) Assignees: Dow Global Technologies LLC, Midland, MI (US); Dow, Portugal Produtos Quimicos, Sociedade Unipessoal, Estarreja (PT)

( * ) Notice: Subject to any disclaimer, the term of this patent is extended or adjusted under 35 U.S.C. 154(b) by 629 days.

(21) Appl. No.: 17/288,967

(22) PCT Filed: Jul. 31, 2019

(86) PCT No.: PCT/US2019/044434
§ 371 (c)(1),
(2) Date: Apr. 27, 2021

(87) PCT Pub. No.: WO2020/091867
PCT Pub. Date: May 7, 2020

(65) Prior Publication Data
US 2021/0403418 A1 Dec. 30, 2021

Related U.S. Application Data

(60) Provisional application No. 62/753,495, filed on Oct. 31, 2018.

(51) Int. Cl.
C07C 263/10 (2006.01)
C07C 263/20 (2006.01)
C07C 273/18 (2006.01)
C08G 18/76 (2006.01)

(52) U.S. Cl.
CPC .......... *C07C 263/10* (2013.01); *C07C 263/20* (2013.01); *C07C 273/1818* (2013.01); *C07C 273/1827* (2013.01); *C07C 273/1881* (2013.01); *C08G 18/7664* (2013.01)

(58) Field of Classification Search
None
See application file for complete search history.

(56) References Cited

U.S. PATENT DOCUMENTS

| | | | |
|---|---|---|---|
| 3,862,973 A | 1/1975 | Dietrich | |
| 3,903,126 A | 9/1975 | Woerner | |
| 4,405,527 A | 9/1983 | Wegener | |
| 4,703,100 A | 10/1987 | Rasshofer | |
| 4,745,216 A | 5/1988 | Keggenhoff | |
| 4,837,359 A | 6/1989 | Woynar | |
| 4,914,236 A * | 4/1990 | Knofel | C07C 209/78 564/334 |
| 5,994,491 A | 11/1999 | Woynar | |
| 2005/0222291 A1 | 6/2005 | Pirkl | |

FOREIGN PATENT DOCUMENTS

| | | |
|---|---|---|
| EP | 1561746 A | 8/2005 |
| EP | 1773755 B | 10/2012 |
| EP | 3564212 A | 6/2019 |
| WO | 2006/022641 A | 3/2006 |
| WO | 2018/124526 A | 7/2018 |

* cited by examiner

*Primary Examiner* — Amy C Bonaparte

(57) ABSTRACT

Monoisocyanate impurities are removed from a process stream obtained when solvent is separated from a polyisocyanate product. The monoisocyanates are reacted with amine compounds at specific molar ratios to produce ureas. The ureas can be discarded by burning, landfilling or otherwise. Alternatively the ureas can be recycled back into the polyisocyanate manufacturing process, where they are formed into biuret compounds that can remain with the polyisocyanate product.

9 Claims, No Drawings

METHOD FOR REMOVING MONOISOCYANATES FROM ORGANIC SOLUTION

This invention relates to methods for removing monoisocyanates from organic solutions.

Polyisocyanates are produced industrially in large volumes. Their primary use is as a raw material for making polyurethane and polyurea polymers.

Monoisocyanates sometimes are produced as a by-product of the manufacturing process. For example, a small amount of phenyl isocyanate is commonly produced when diphenylmethane diisocyanate (MDI) or polymeric MDI is manufactured. "Polymeric MDI" is a mixture of one or more isomers of MDI and one or more polymethylene polyphenylisocyanates that have at least three phenyl isocyanate groups.

These monoisocyanates are usually removed from the product. In the case of MDI or polymeric MDI, phenyl isocyanate is often removed when the product is separated from the reaction solvent. This produces a stream that contains solvent, most of the phenyl isocyanate and a small quantity of MDI or polymeric MDI.

The solvent is generally recycled, but to do so the monoisocyanate must be removed from it so the monoisocyanate does not accumulate over time. In the case of phenyl isocyanate in particular, removal and destruction of that compound is important because of potential toxicological concerns.

Therefore, an effective and inexpensive method for removing monoisocyanates from a solvent stream is wanted.

Some previous approaches have capitalized on the reactivity of isocyanate groups to convert the monoisocyanate to a solid material that is easily separated from the solvent. Thus, EP 1,773,755 describes catalyzing the trimerization of phenyl isocyanate to form tris(phenyl)isocyanurate. U.S. Pat. No. 4,745,216 describes reacting the phenyl isocyanate with polymer beads that have amino or hydroxyl functionality. U.S. Pat. No. 4,405,527 describes reacting the phenyl isocyanate with stoichiometric or greater amounts of polyamine or glycols to convert it to urethanes or ureas.

All of these approaches have significant shortcomings. There is the cost of added raw materials. These added raw materials represent another source of impurities which themselves must be rigorously removed from the solvent before it is recycled, again to avoid accumulation. Water is inexpensive but tends to lead to a slow reaction with low conversions of the monoisocyanates to ureas and also tends to produce monoamine by-products, which are another source of contamination. Adding stoichiometric or greater amounts polyamines as in U.S. Pat. No. 4,405,527 can be especially problematic because they often are not entirely consumed or removed. When these polyamines are recycled with the solvent, they engage in unwanted reactions that in some cases consume the desired polyisocyanate products, decreasing yield and forming higher molecular weight impurities that increase viscosity and modify other characteristics of the product, and if left in the product, they present a difficult separation problem if they are to be removed. The unreacted polyamines also can become phosgenated to form unwanted polyisocyanate species that are very difficult to remove from the desired product. In addition, adding certain polyamines often rapidly produces a thick slurry of the corresponding polyureas that is very difficult to handle at industrial scale.

This invention is a method for removing organic monoisocyanates from an organic solvent. The method comprises:

a) contacting i) a starting solution containing at least 85 weight percent, based on the weight of the starting solution, of one or more organic solvents inert to reaction with isocyanate and amine groups and up to 15 weight percent, based on the weight of the starting solution, of organic isocyanate compounds that include at least one monoisocyanate, with ii) at least one amine, soluble in the one or more organic solvents, the amine having at least one primary or secondary amino group, in proportions sufficient to provide 0.01 to 0.80 equivalents of primary and/or secondary amino groups per equivalent of isocyanate groups in the starting solution; and b) reacting at least a portion of the monoisocyanate with at least a portion of the amine to form one or more urea compounds.

This process produces urea compounds, including urea compounds that correspond to a reaction product of the monoisocyanate and the amine compound.

Good conversions of the monoisocyanate compounds are achieved with short reaction times. The reaction tends to produce thin slurries that remain easily stirrable and easily handled. This allows one to maintain the urea compounds in solution or suspension in the liquid phase until the reaction mixture is transferred for further processing. This represents a major advantage over processes such as are described, for example, in U.S. Pat. No. 4,405,527.

In addition, the urea compounds formed in this process often can be recycled back into the isocyanate-manufacturing process with little if any adverse effect on the process or the product so produced. Those urea compounds can form biuret compounds under the conditions of certain steps of the isocyanate-manufacturing process. It has been found that those biuret compounds in many cases can be left in the product isocyanate with very little effect on its properties, isocyanate functionality and utility. This is particularly the case when the amine is a monoamine, which produces low molecular weight ureas as it reacts in step b) of the process.

Therefore, some embodiments of the invention further comprise a step of reacting one or more urea compounds produced in step b) with an excess of a polyisocyanate to produce a biuret-modified polyisocyanate composition.

In alternative embodiments, the process comprises a step of separating at least a portion of the one or more organic solvents from the one or more urea compounds formed in step b).

In particular embodiments, the invention is an MDI and/or polymeric MDI manufacturing process, comprising the steps of:

a) reacting aniline with formaldehyde in a solvent to produce a mixture of MDA, PMDA and unreacted aniline in the solvent;

b) distilling aniline from the mixture produced in step a) to produce a process stream containing the solvent, MDA, PMDA and residual aniline;

c) phosgenating the process stream from step b) to form an isocyanate process stream containing the solvent, MDI, one or more polymethylene polyphenylisocyanates that have at least three phenyl isocyanate groups and phenyl isocyanate;

d) separating MDI, polymethylene polyphenylisocyanates that have at least three phenyl isocyanate groups and phenyl isocyanate from the isocyanate process stream obtained in step c) by distillation to produce a solvent stream containing solvent, 0.2 to 10 weight percent phenyl isocyanate based on the weight of the solvent stream and 0.0001 to 5 weight percent, based on the weight of the solvent stream, of MDI and/or one or more polymethylene polyphenylisocyanates that have at least three phenyl isocyanate groups;

e) combining the solvent stream obtained in step d) with aniline at a ratio of 0.01 to 0.8 moles of aniline per mole of phenyl isocyanate and reacting at least a portion of the aniline with phenyl isocyanate to form urea compounds;

f) reacting at least a portion of the urea compounds with a polyisocyanate to form biuret compounds.

The starting solution contains one or more organic solvents. The solvent is generally characterized as being (i) a solvent for the monoisocyanate and the amine compound, (ii) devoid of isocyanate groups and (iii) inert, i.e., non-reactive toward isocyanate groups and amino groups under the conditions of the process. Examples of suitable solvents include halogenated aromatics such as monochlorobenzene, o-dichlorobenzene, p-dichlorobenzene and m-dichlorobenzene, various trichlorobenzene isomers, mixtures thereof, and the like. Other suitable solvents include, for example, benzene, toluene, para-xylene, and various aliphatic hydrocarbons that are halogenated or non-halogenated, mixtures of any two or more thereof, and the like.

The starting solution contains at least one monoisocyanate. The monoisocyanate is an organic compound, soluble in the solvent(s), that contains exactly one isocyanate group. It preferably is a liquid or solid at room temperature. The isocyanate group may be bonded to an aliphatic (including cycloaliphatic) or aromatic carbon atom. Specific examples are phenyl isocyanate, p-chloromethylphenyl isocyanate, o-chloromethylphenyl isocyanate, and toluene monoisocyanate.

The starting solution may contain one or more polyisocyanates. The polyisocyanate is an organic compound, soluble in the solvent(s), that contains at least 2 isocyanate groups. The isocyanate group may be bonded to an aliphatic (including cycloaliphatic) or aromatic carbon atom. Specific examples are diphenylmethane diisocyanates (including the 4,4'-, 2,4'- and/or 2,2'-isomers), polymethylene polyphenylisocyanates that have at least three phenyl isocyanate groups, and toluene diisocyanates.

The organic solvent(s) constitute at least 85% of the weight of the starting solution. In particular embodiments, the organic solvent(s) may constitute at least 90% of the weight of the starting solution, and may constitute up to 95%, up to 99.8%, up to 99.5%, up to 99% or up to 98.5% thereof.

The monoisocyanate(s) may constitute up to 15% of the weight of the starting solution. The monoisocyanate(s) constitute at least 0.2%, at least 0.5%, at least 1% or at least 1.5% of the weight of the starting solution, and may constitute up to 10%, up to 7.5%, up to 5%, up to 4%, or up to 3% thereof.

The polyisocyanate(s) may constitute up to 5% of the weight of the starting solution. The polyisocyanate(s), if present at all, may constitute at least 0.0001%, at least 0.1%, at least 0.2%, at least 0.5%, at least 1% or at least 1.5% of the weight of the starting solution, and may constitute up to 5%, up to 4%, or up to 3% thereof.

The starting solution may be or include a process stream from a polyisocyanate manufacturing facility. Polyisocyanates are sometimes manufactured by reacting a polyamine with phosgene in solution. Upon separation of the solvent from the polyisocyanate product, a process stream is sometimes produced that contains, in addition to the solvent, small quantities of monoisocyanates and in some cases small quantities of polyisocyanates.

In a particular embodiment, the process stream is taken from a diphenylmethane diisocyanate (MDI) production facility. MDI and polymeric MDI are made industrially by condensing aniline with formaldehyde to ultimately produce methylene dianiline (MDA) and/or polymethylene polyanilines that have 3 or more aniline groups (PMDA), which are then reacted with phosgene in solution to produce the corresponding polyisocyanates. A small amount of unreacted aniline becomes phosgenated to produce phenyl isocyanate. When the product is separated from the reaction solvent, a process stream is produced that contains the solvent, a small quantity of phenyl isocyanate and a small quantity of MDI and/or higher polymethylene polyphenylisocyanates. This process stream is a useful starting solution for the process of this invention.

The amine compound is characterized in that it is soluble in the solvent(s) of the starting solution and has at least one primary or secondary amino group. The amino group(s) may be bonded to aliphatic (including cycloaliphatic) or aromatic carbon atoms. The amine compound(s) may contain up to 10, up to 6 or up to 4 primary and/or secondary amino groups.

The amine compound preferably is a room temperature liquid or solid. The amine compound may have a molecular weight of, for example at least 80 or at least 90 up to 1500, up to 1200, up to 1000, up to 800 or up to 500 or up to 350. Examples of useful amine compounds include 2,2'-methylenedianiline; 2,4'-methylenedianiline; 4,4'-methylenedianiline; 2,4-toluene diamine; 2,6-toluene diamine; one or more PMDAs which contain 3 to 10, especially 3 to 6, phenylamine groups, and the like. Mixtures of any two or more of the foregoing are useful.

A preferred monoamine compound is aniline. Another preferred amine compound is a mixture of 2,4'- and 4,4'-methylene dianiline, which mixture may further contain 2,2'-methylene dianiline.

Another preferred amine compound is a mixture of at least one diamine and at least one polyamine compound having 3 to 10 primary and/or secondary amino groups. Such a mixture may contain, for example, 30 to 80 weight percent based on the weight of the amine mixture of one or more diamine compounds and 20 to 70 weight percent of the polyamine(s). An especially preferred mixture of this type is a mixture of 30 to 80 weight percent of one or more isomers of MDA and 20 to 70 weight percent of one or more PMDAs that contain 3 to 10, especially 3 to 6, aniline groups. Mixtures of MDA and PMDA are sometimes referred to herein as "polymeric MDA".

It is also preferred that the amine (as well as the starting solution and reaction mixture formed therefrom) is essentially devoid of water. For purposes of this invention, an amine compound or starting solution is considered as being essentially devoid of water if it contains no more than 0.05 wt. % thereof, based on the total weight thereof. The amine and starting solution each preferably contain no more than 0.01 wt. % of water.

In the process of the invention, the starting solution and amine compounds are contacted in proportions sufficient to provide 0.01 to 0.8 equivalents of primary and/or secondary amino groups per equivalent of isocyanate groups in the starting solution. In some embodiments, at least 0.1, at least 0.6, at least 0.4 or at least 0.5 equivalents of primary and/or secondary amino groups are provided per equivalent of isocyanate groups in the starting solution. One mole of primary amino groups is considered as one equivalent thereof for purposes of calculating this equivalent ratio.

The amine compound can be contacted with the starting solution by adding the amine compound all at once, or in two or more increments (such as at least 3 or at least 4 increments and up to 10, up to 8 or up to 6 increments) or even continuously. When the amine compound is added in two or more increments or continuously, in some embodiments, the amine compound may be added such that (i) the total amount of amine compound added in all increments combined is such that 0.01 to 0.8 equivalents of primary and/or secondary amino groups are added per equivalent of isocyanate groups in the starting solution and (ii) the instantaneous ratio of equivalents of primary and/or secondary amino groups provided by the amine compound to equivalents of isocyanate groups in the reaction mixture is maintained at 0.6:1 or less, preferably 0.5:1 or less. The "instantaneous" ratio refers to the ratio at any specific point in time during the steps of combining the amine compound and starting solution and performing the subsequent reaction to form urea compounds.

The amine compound is added in increments, the increments can be separated by a reaction period of, for example, 30 seconds to 60 minutes, 1 minute to 30 minutes, or 5 minutes to 20 minutes.

The contacting step can be performed at a temperature of, for example, 0° C. to 275° C. In some embodiments, the contacting step is performed at a temperature of at least 5° C., at least 15° C. or at least 20° C. In other embodiments, the contacting step is performed at an elevated temperature such as at least 50° C., at least 70° C., at least 80° C., at least 90° C. or at least 100° C. A preferred upper temperature is up to 225° C., up to 200° C., up to 180° C., up to 160° C. or up to 140° C.

After contacting, at least a portion of the monoisocyanate reacts with at least a portion of the amine compounds to form one or more urea compounds in the one or more organic solvents. This reaction often commences as soon as the starting solution and amine compound(s) are combined, even at the lower contacting temperatures mentioned above. Even when the contacting step is performed at a somewhat lower temperature (such as 50° C. or below), it is often beneficial to heat the reaction mixture to a higher temperature after the starting solution and amine compound(s) have been combined. This higher temperature may be, for example, at least 50° C., at least 70° C., at least 80° C., at least 90° C. or at least 100° C. and, for example, up to 250° C., up to 225° C., up to 200° C., up to 180° C., up to 160° C. or up to 140° C., to obtain faster reaction rates and/or more complete reaction. In some embodiments, the higher temperature may be a reflux temperature of the solvent(s).

The reaction can be performed over a wide range of pressures from subatmospheric to superatmospheric. The pressure should be high enough such that the amine(s), monoisocyanate and solvent do not volatilize at the reaction temperature.

The reaction step (b) may take as little as about 1 minute to 8 hours or more. In general, longer reaction times favor more complete consumption of the amine compound(s), although most of the consumption of the monoisocyanate tends to take place rapidly, in the first few minutes of the reaction, as illustrated in the examples that follow. A preferred reaction time is at least 5 minutes or at least 10 minutes up to about 2 hours or up to about 1 hour.

In some embodiments the reaction step is continued until the concentration of amine compound(s) in the reaction mixture is reduced to 0.01% by weight or less, based on the total weight of the reaction mixture (starting solution plus amine compound(s)). This is not necessary, however, and the reaction may be discontinued while larger amounts of the amine compound(s) remain. It has been found, surprisingly, that in embodiments in which the amine compound is or includes aniline and the monoisocyanate is or includes phenyl isocyanate, the aniline in some cases is not all consumed in the reaction step and accordingly in such a case somewhat larger amounts, such as up to 0.05% by weight or up to 0.03% by weight, may remain after the reaction step has been completed. Complete consumption of the aniline is favored by (i) adding the aniline to the starting solution in two or more increments and/or continuously as described above and/or (ii) combining the aniline with the starting solution at a temperature of at least 80° C. or at least 90° C., especially 90 to 130° C. MDA and PMDA, on the other hand, tend to react fully with complete consumption of those amines, even when combined with the starting solution all at once, and/or when combined with the starting solution at lower temperatures.

The reaction of the amine compound(s) with the monoisocyanate produces one or more urea compounds. These urea compound(s) are often solids that are partially to fully insoluble in the solvent (at least at room temperature), although in some cases, such as that in which the urea compound is a reaction product of phenyl isocyanate and aniline, some or all of the urea compounds may be soluble in the solvent(s). The formation of solids produces a slurry. An advantage of the invention is that the slurry remains somewhat thin and easily stirrable. As such, the particles of urea compounds are easily kept in suspension using agitation or other mechanical methods. This promotes easy handling and material transfer using simplified industrial equipment.

Monoisocyanates are consumed by reaction with the amine compounds, thereby reducing the quantity of monoisocyanates in the reaction mixture. The quantity of monoisocyanates may be reduced by, for example, at least 20%, at least 40%, at least 50% or at least 75%, relative to the amount in the starting solution. Polyisocyanate compounds, if present in the starting solution, also may be consumed by reaction with the amine mixture. In such a case the quantity of those materials also will be reduced in the reaction step.

In some embodiments of the invention, at least a portion of the one or more organic solvents is separated from the one or more urea compounds. Solid-liquid separation methods such as decantation, filtration or centrifugation are suitable. The organic solvent, after separation from some or all of the urea compounds, contains a reduced amount of monoisocyanate compound(s). In an industrial polyisocyanate manufacturing setting, this separated organic solvent may be recycled back into polyisocyanate manufacturing process at any point downstream of the phosgenation reaction, and/or recycled back into the process of this invention.

The urea compounds separated from the organic solvent may be discarded, burned or otherwise disposed of. By converting monoisocyanates to urea compounds, toxicological and other concerns associated with the handing and disposal of the monoisocyanates are at least partially alleviated.

The urea compounds under certain conditions can react with isocyanate compounds to form biuret compounds. Therefore, in some embodiments of the invention, the urea compound(s) are combined with a polyisocyanate and caused to react with the polyisocyanate to produce a composition that contains one or more biuret compounds that correspond to the reaction product of one or more of the urea compound(s) and the polyisocyanate.

Suitable conditions for biuret formation include an elevated temperature, such as at least 100° C. or at least 120° C. and, for example, up to 230° C. or up to 200° C. A reaction time of 1 to 300 minutes is generally suitable, and a more preferred reaction time is 1 to 120 minutes or 5 to 60 minutes. Pressures may be superatmospheric, atmospheric or subatmospheric.

Such a biuret-forming reaction is conveniently performed by recycling the organic solvent containing the urea compounds back into the isocyanate manufacturing process, at any point downstream of the phosgenation step. An isocyanate manufacturing process often includes a step of separating the isocyanate product from the process solvent. This separation is often performed by distillation, which distillation conditions typically include temperature and other conditions suitable for biuret formation.

Accordingly, in one embodiment of the process, the organic solvent containing the urea compounds is recycled into the isocyanate manufacturing process, and the resulting process stream containing process solvent (including the recycled solvent), isocyanate compounds and urea compounds is subjected to a distillation step. The distillation step is performed at a temperature as described above with regard to the biuret-forming step, such that biuret formation and polyisocyanate product recovery from the process solvent are achieved simultaneously. This distillation step may be performed at a subatmospheric pressure. This results in a substantially solvent-free polyisocyanate composition containing biuret structures and a distillate stream containing solvent, which distillate stream typically will contain a small amount of monoisocyanate(s) and possibly polyisocyanates that distill with the solvent.

Additionally, the biuret-forming reaction may be performed in a separate reactor external to the isocyanate manufacturing process. The biuret-modified isocyanate product then can be introduced back into the isocyanate manufacturing process. The separate biuret-forming reaction may be either a batch reaction or a continuous reaction.

The weight ratio of urea compounds to isocyanate compounds should be low, such as 0.001 to 5 parts by weight of urea compounds per 100 parts by weight of isocyanate compounds. A more preferred amount is 0.005 to 2.5 parts or 0.01 to 1.5 parts, on the same basis.

When the urea compounds are to be recycled in the manner just described, it is preferred that the amine compound is a monoamine such as aniline. Urea compounds made in a reaction of a monoamine with a monoisocyanate tend to have lower molecular weights, and form lower molecular weight biuret compounds.

In a particular embodiment, the starting solution is a process stream from a MDI and/or polymeric MDI manufacturing facility. Such a production facility includes a phosgenation unit in which phosgene is reacted with MDA and/or a mixture of MDA with one or more PMDAs to produce the polyisocyanate compounds. Such a production facility may also include an upstream unit in which aniline and formaldehyde are reacted to produce the MDA and/or PMDA. In such a production facility, the aniline is typically present in excess, and the excess is distilled from the product and recycled. Small amounts of aniline that are not removed in the distillation step are introduced into the phosgenation unit and converted to phenyl isocyanate. When the solvent is separated from the MDI and/or polymeric MDI, a process stream is formed in which all or a portion of the phenyl isocyanate is concentrated in the solvent. In these embodiments, this process stream forms a starting solution for use in the urea-forming process of this invention.

Such a process stream includes the organic solvent (which is preferably a chlorinated benzene compound), phenyl isocyanate and optionally but typically a small amount of 2,4'-, 4,4'- and/or 2,2'-MDI. The phenyl isocyanate content may be 0.05 to 10% by weight and is more typically 0.1 to 5% by weight, based on the weight of the process stream, and the MDI may constitute up to 5% by weight on the same basis.

In this particular embodiment, the amine compound may be aniline, MDA (2,4'-, 4,4'- and/or 2,2'-isomers), or a mixture of MDA (2,4'-, 4,4'- and/or 2,2'-isomers) with one or more PMDAs. In cases in which the amine compound is aniline, it is preferred to recycle the urea compounds that form (optionally with the process solvent) back into the isocyanate-manufacturing process, at any point downstream of the phosgenation step, for biuret formation as described before. Biuret formation preferably is performed during a flashing and/or distillation step in which the MDI and/or polymeric MDI is separated from the process solvent. In cases in which the amine compound is MDA and/or PMDA, it is preferred to separate the urea compounds from the solvent rather than to recycle them into the isocyanate production process, although the latter can be done if desired. The organic solvent after separation from the urea compounds is conveniently recycled back into the process at any point of the isocyanate manufacturing process downstream of the phosgenation.

Alternatively, the biuret formation may also be performed in an external reaction, as a batch reaction or continuous reaction, as discussed above.

Ureas formed by reaction of phenyl isocyanate and aniline in accordance with the invention, when recycled into the MDI and/or PMDI manufacturing process in small amounts as described above, produce biuret-containing isocyanate products that can be used in the same manner as the unmodified MDI and/or PMDI products. Depending on the amount of ureas recycled into the MDI and/or PMDI, product viscosities may be increased slightly. Molecular weights ($M_n$, $M_w$, $M_z$) and polydispersities (all as measured by GPC against 1000 molecular weight polyethylene glycol standards) all tend to increase slightly. Isocyanate content and functionality usually decrease slightly. Generally, when less than about 0.5 part by weight of urea compounds per 100 parts by weight of isocyanate compounds are recycled, no significant change in the properties, utility or performance of the biuret-containing isocyanate products is detected.

The following examples are provided to illustrate the invention, but are not intended to limit the scope thereof. All parts and percentages are by weight unless otherwise indicated.

COMPARATIVE SAMPLES A AND B

Stock solutions are prepared to emulate a process stream obtained from a polymeric MDI production facility after separation of the polyisocyanate product from the reaction solvent. The stock solution contains 0.05% of a mixture of the 2,4'- and 4,4'-isomers of MDI, approximately 2% phenyl isocyanate (exact amounts as measured by high pressure chromatography reported below) and the balance, monochlorobenzene.

Comp. Sample A

Under nitrogen and with stirring, a quantity of the stock solution is combined at room temperature with 4,4'-diaminodiphenyl methane (MDA) at a ratio of 1 equivalent of isocyanate groups to 1 equivalent of amino groups. A thick, barely stirrable white slurry forms within about 2 minutes. This slurry is heated to reflux, refluxed for 8 minutes and then cooled to room temperature. The phenyl isocyanate concentration is reduced from 2.15% to 0.044%. However, the slurry that forms is too thick to handle in most industrial equipment.

Comp. Sample B

Comparative Sample A is repeated, except this time the stock solution is diluted with more monochlorobenzene in a 1:19 ratio prior to being combined with the MDA. This reduces the phenyl isocyanate concentration to about 0.1 percent. The amount of MDA is reduced proportionately. Heating to reflux is begun immediately and reflux is achieved after 16 minutes. Samples are taken at that time and periodically thereafter for analysis by high pressure liquid chromatography (HPLC). Particles do not form until about 30 minutes after the reaction mixture is brought to reflux. Results are as indicated in Table 1:

TABLE 1

| Reaction Time (minutes) | Phenyl Isocyanate Concentration, % | MDI concentration, % |
|---|---|---|
| 0 | 0.1 | 0.0025 |
| 16 (Start of Reflux) | 0.1 | None detected |
| 106 | 0.09 | None detected |
| 166 | 0.06 | None detected |
| 346 | 0.03 | None detected |

By diluting the system, the problem of a thick slurry can be avoided. However, as the data in Table 1 shows, MDA reacts every slowly with phenyl isocyanate in such a dilute system. Approximately three hours are needed to reduce the amount of phenyl isocyanate by half.

EXAMPLES 1-3 AND COMPARATIVE SAMPLES C AND D

Comp Sample C

Under nitrogen and with stirring, a quantity of the stock solution is combined at room temperature with aniline at a ratio of 1 equivalent of isocyanate groups to 1 equivalent of amino groups. A thick, barely stirrable white slurry forms within 1 minute. This slurry is heated to reflux. 106 minutes after the aniline and stock solution are combined, another 0.49 equivalent of aniline per starting equivalent of isocyanate groups is added and refluxing is continued. Samples are taken thereafter for analysis. Results are as indicated in Table 2:

TABLE 2

| Reaction Time (minutes) | Phenyl Isocyanate Concentration, % | Aniline Concentration, % | Comment |
|---|---|---|---|
| 0 | 2.1 | | |
| 10 | 0.4 | 0.30 | Start of reflux |
| 40 | 0.2 | 0.24 | |
| 70 | 0.07 | 0.08 | |
| 136 | 0.03 | 0.8 | Additional aniline added after 106 minutes |
| 223 | 0.02 | 0.9 | |

As the data in Table 2 shows, good conversion of phenyl isocyanate is seen but aniline is not all consumed. In addition, the thick slurry can be processed only with difficulty. Unreacted phenyl isocyanate is present even after further addition of aniline.

Example 1

Under nitrogen and with stirring, a quantity of the stock solution at reflux is combined with aniline (also at reflux) at a ratio of 1 equivalent of isocyanate groups to 0.62 equivalent of amino groups. This slurry is maintained at reflux. The refluxing solution turns hazy after 20 minutes at reflux. Samples are taken periodically for analysis. Gas chromatography-mass spectrometry on the product at 167 minutes (final product) confirms the presence of the unreacted aniline. Results are as indicated in Table 3:

TABLE 3

| Reaction Time (minutes) | Phenyl Isocyanate Concentration, % | Aniline Concentration, % |
|---|---|---|
| 0 | 1.86 | 0 |
| 1 | 1.34 | 0.48 |
| 24 | 0.56 | 0.01 |
| 167 | 0.58 | 0.01 |

The urea compounds produced in the foregoing reaction are recovered by vacuum filtration and dried under vacuum (100° C./16 hours) until a constant weight is obtained. Under nitrogen, 0.3 gram of the urea compounds are combined with 29.7 grams of a polymeric MDI (2.7 average isocyanate functionality, 134 isocyanate equivalent weight), heated with stirring to 100° C. over 12 minutes and held at that temperature for 22 minutes. The temperature is then increased over 6 minutes to 125° C. and held at that temperature for an hour. The isocyanate equivalent weight of the biuret-containing product is measured by titration. Matrix-Assisted Laser Desorption/Ionization Mass Spectral (MALDI-TOF MS) analysis confirms the presence of biuret structure.

For comparison, the polymeric MDI by itself is subjected to the same handling and heating profile.

The viscosity of the biuret-containing product and the heated polymeric MDI each are measured on a plate-and-cone rheometer at 25.6° C., with a 40 mm cone and a 54 μm gap. Molecular weights are measured on each by GPC against a 1000 MW polyethylene glycol standard, using a 1% w/v solution in anhydrous methanol.

Results of the foregoing testing are as indicated in Table 4.

TABLE 4

| Sample | Ex. 1 | Heat-treated Polymeric MDI |
|---|---|---|
| Isocyanate equivalent weight | 134.7 | 132.8 |
| Viscosity, Pa · s | 0.24 | 0.21 |
| $M_n$ | 456 | 451 |
| $M_w$ | 584 | 573 |
| MP | 332 | 332 |
| $M_z$ | 855 | 823 |
| Polydispersity | 1.28 | 1.27 |

As the data in Table 4 shows, the biuret-modified polymeric MDI has properties that are minimally changed from those of the unmodified isocyanate product.

Example 2

Example 1 is repeated, this time reducing the amount of aniline further so as to provide only 0.495 equivalent of amino groups per equivalent of isocyanate groups. A thin, easily stirrable slurry forms after about 1 minute. Samples are taken periodically for analysis with results as indicated in Table 5:

TABLE 5

| Reaction Time (minutes) | Phenyl Isocyanate Concentration, % | Aniline Concentration, % |
|---|---|---|
| 0 | 2.05 | 0 |
| 12 (start of reflux) | 1.1 | 0.03 |
| 72 | 1.1 | 0.04 |
| 192 | 1.2 | 0.04 |

Example 3

Example 1 is repeated, this time reducing the amount of aniline still further so as to provide only 0.256 equivalent of amino groups per equivalent of isocyanate groups. A thin, easily stirrable slurry forms after about 4 minutes. Samples are taken periodically for analysis with results as indicated in Table 6:

TABLE 6

| Reaction Time (minutes) | Phenyl Isocyanate Concentration, % | Aniline Concentration, % |
|---|---|---|
| 0 | 2.1 | 0 |
| 11 (start of reflux) | 1.4 | 0.02 |
| 71 | 1.6 | 0.03 |
| 131 | 1.7 | 0.02 |

Comp. Sample D

Example 1 is repeated again, this time reducing the amount of aniline still further so as to provide only 0.099 equivalent of amino groups per equivalent of isocyanate groups. Particles are not seen in the refluxing solution until samples are removed and cooled for analysis. 1,3-Diphenylurea is observed in the gas chromatographic analyses starting with the sample from the 13 minute reaction time. Results of periodic analysis are as indicated in Table 7:

TABLE 7

| Reaction Time (minutes) | Phenyl Isocyanate Concentration, % | Aniline Concentration, % |
|---|---|---|
| 0 | 2.1 | 0 |
| 13 (start of reflux) | 1.9 | 0.04 |
| 73 | 1.9 | 0.03 |
| 433 | 2.0 | 0.02 |

Only a minor amount of the phenyl isocyanate is removed, and aniline still remains in the product.

EXAMPLE 4

Under nitrogen and with stirring, a quantity of the stock solution is combined at room temperature with aniline and a polymeric MDA at a ratio of 1 equivalent of isocyanate groups to 0.045 equivalent of aniline and 0.205 equivalent of polymeric MDA. The polymeric MDA contains about 40-45 weight-% methylene dianiline (o,o'-, o,p'- and p,p'-isomers). The remaining 55-60 weight-% are oligomers that have 3 or more aniline groups. This polymeric MDA contains 9.835 milliequivalents nitrogen per gram and 0.0305 milliequivalent tertiary amine per gram.

A thin white slurry forms within 1 minute. This slurry is heated to reflux. Samples are taken periodically thereafter for analysis. HPLC analysis of a sample from 376 minutes of reaction reveals that no polymeric MDI is present. Results are as indicated in Table 8:

TABLE 8

| Reaction Time (minutes) | Phenyl Isocyanate Concentration, % | Aniline Concentration, % |
|---|---|---|
| 0 | 2.2 | |
| 16 (start of reflux) | 1.7 | 0.02 |
| 46 | 1.7 | 0.02 |
| 256 | 1.7 | 0.03 |
| 376 | 1.8 | 0.03 |

COMPARATIVE EXAMPLES E AND F

Comp. Ex. E

Under nitrogen and with stirring, a quantity of the stock solution is combined at room temperature with water at a ratio of 1 equivalent of isocyanate groups to 0.262 equivalent of water. This slurry is heated to reflux. Samples are taken periodically thereafter for analysis. The reaction solution remains transparent throughout the reaction. Results are as indicated in Table 9:

TABLE 9

| Reaction Time (minutes) | Phenyl Isocyanate Concentration, % | Aniline Concentration, % |
|---|---|---|
| 0 | 2.1 | |
| 15 (start of reflux) | 2.1 | 0.013 |
| 75 | 2.2 | 0.011 |
| 315 | 2.2 | 0.012 |

Comp. Ex. F is performed in the same manner, except the ratio of isocyanate to water is 1:0.252 and heating is only to 80° C. The reaction solution again remains transparent throughout the reaction. Results are as indicated in Table 10:

TABLE 10

| Reaction Time (minutes) | Phenyl Isocyanate Concentration, % | Aniline Concentration, % |
|---|---|---|
| 0 | 2.1 | |
| 11 (start of reflux) | 2.1 | 0 |
| 71 | 2.1 | 0 |
| 311 | 2.2 | 0 |

Comparative Samples E and F show the effect of using water to attempt to remove phenyl isocyanate. Very little conversion of the phenyl isocyanate is seen and, at reflux, very little aniline is produced.

EXAMPLES 5-9

Ex. 5

Under nitrogen and with stirring, a quantity of the stock solution is combined at room temperature with a polymeric MDA as described in previous examples, at a ratio of 1 equivalent of isocyanate groups to 0.250 equivalent of polymeric MDA. A thin white slurry forms as soon as the stock solution and polymeric MDA are combined. This slurry is heated to reflux. Samples are taken periodically thereafter for analysis. No polymeric MDA is detected by HPLC analysis after 378 minutes of reaction time. Results are as indicated in Table 11:

TABLE 11

| Reaction Time (minutes) | Phenyl Isocyanate Concentration, % |
|---|---|
| 0 | 2.1 |
| 18 (start of reflux) | 1.6 |
| 78 | 1.6 |
| 378 | 1.6 |

About 25% of the phenyl isocyanate is removed rapidly in this process, with complete consumption of polymeric MDA. In addition, the slurry remains easily stirrable and can be processed without difficulty at industrial scale.

Ex. 6

Example 5 is repeated except an equivalent ratio of 1 equivalent of isocyanate groups to 0.502 equivalent of polymeric MDA is used. As with Ex. 5, a thin, easily stirrable slurry forms immediately upon contacting the stock solution and polymeric MDA. No polymeric MDA is detected by HPLC analysis by 196 minutes of reaction time. Results of periodic analysis are indicated in Table 12.

TABLE 12

| Reaction Time (minutes) | Phenyl Isocyanate Concentration, % |
|---|---|
| 0 | 2.0 |
| 16 (start of reflux) | 1.1 |
| 76 | 1.0 |
| 196 | 1.0 |

By increasing the amount of polymeric MDA to about one half equivalent per equivalent of isocyanates, a greater amount of phenyl isocyanate is removed. Again, complete removal of polymeric MDA is seen and the slurry remains thin and easily handled.

Ex. 7

Example 5 is repeated again except an equivalent ratio of 1 equivalent of isocyanate groups to 0.681 equivalent of polymeric MDA is used. Once again, a thin, easily stirrable slurry forms immediately upon contacting the stock solution and polymeric MDA. Results of periodic analysis are indicated in Table 13. No polymeric MDA is detected by HPLC analysis after 47 minutes of reaction time or thereafter.

TABLE 13

| Reaction Time (minutes) | Phenyl Isocyanate Concentration, % |
|---|---|
| 0 | 2.0 |
| 17 (start of reflux) | 0.8 |
| 47 | 0.6 |
| 77 | 0.6 |
| 257 | 0.6 |

By increasing the amount of added amine to 0.681 equivalent per equivalent of isocyanates, about 70% of the phenyl isocyanate is consumed, with complete consumption of polymeric MDA. The slurry is thin and easily processed.

Ex. 8

Under nitrogen and with stirring, a quantity of the stock solution is heated to reflux. Separately, a quantity of a 3.3%-wt. solution of the polymeric MDA in chlorobenzene is heated to reflux. The refluxing solutions are combined at a ratio of 1 equivalent of isocyanate groups to 0.638 equivalent of amino groups and held at reflux. Once again, a thin, easily stirrable slurry forms within about 30 seconds. Results of periodic analysis are indicated in Table 14. No polymeric MDA is detected by HPLC analysis after one minute of reaction time or at any later time.

TABLE 14

| Reaction Time (minutes) | Phenyl Isocyanate Concentration, % |
|---|---|
| 0 | 1.8 |
| 1 | 0.9 |
| 21 | 0.5 |
| 71 | 0.5 |
| 157 | 0.5 |

In this experiment, over half the phenyl isocyanate is removed within one minute of reaction time. Almost 75% is removed within 21 minutes, with complete consumption of polymeric MDA. The slurry is thin and easily processed.

The urea compounds are removed from the solvent and dried as described in Example 1. 0.3 gram of the urea compounds are combined with 29.7 grams of a polymeric MDI (2.7 average isocyanate functionality, 134 isocyanate equivalent weight) and heated as described in Example 1. The properties of the resulting biuret-modified polyisocyanate are as indicated in Table 15. The properties of the starting polyisocyanate, similarly handled and heat-treated, are again provided for purposes of comparison.

TABLE 15

| Sample | Ex. 1 | Heat-treated Polymeric MDI |
|---|---|---|
| Isocyanate equivalent weight | 134.8 | 132.8 |
| Viscosity, Pa · s | 0.29 | 0.21 |
| $M_n$ | 460 | 451 |
| $M_w$ | 596 | 573 |
| MP | 333 | 332 |
| $M_z$ | 881 | 823 |
| Polydispersity | 1.30 | 1.27 |

As before, the biuret-modified polymeric MDI has properties that are only slightly changed from those of the unmodified isocyanate product.

Ex. 9

Example 5 is repeated again, except the equivalent ratio of 1 equivalent of isocyanate groups to 0.543 equivalent of polymeric MDA is used, and the reaction mixture is stirred at room temperature instead of being heated to reflux. A solution forms which becomes a thin, easily stirrable slurry forms after about 3 minutes. Results of periodic analysis are indicated in Table 16. No polymeric MDA is detected by HPLC analysis at 338 minutes of reaction time.

TABLE 16

| Reaction Time (minutes) | Phenyl Isocyanate Concentration, % |
|---|---|
| 0 | 1.9 |
| 4 | 1.6 |
| 27 | 1.1 |
| 84 | 1.0 |
| 338 | 1.0 |

Even at room temperature, almost half the phenyl isocyanate is removed in 84 minutes of reaction time. Complete removal of polymeric MDA is observed when sampled at 338 minutes. The thin slurry is easily handled in industrial equipment.

EXAMPLES 10A AND 10B

Ex. 10A

A solution of 98% monochlorobenzene, 1.89% phenyl isocyanate and 0.11 wt. % MDI is combined with neat aniline in an amount to provide 0.7 equivalent of amino groups per equivalent of isocyanate groups. The resulting reaction mixture is heated at reflux for 2 hours and cooled to room temperature.

The reaction mixture is then vacuum filtered on a fritted glass funnel (10-16 micron pore size) to remove precipitated urea compounds. 4.23 grams of urea compounds are recovered.

Ex. 10B

Example 10A is repeated without filtering off the urea compounds. Instead, the reaction mixture is rotoevaporated to remove the solvent, leaving the urea compounds behind. 5.65 grams of dry urea compounds are obtained.

These results indicate that filtration only removes about 75% of the urea compounds.

EXAMPLE 11

Under a nitrogen atmosphere, a 2% solution (197.12 grams) of phenyl isocyanate (33.33 milliequivalents) in chlorobenzene is added to a 3 neck, 500 milliliter, round bottom, glass reactor equipped with a chilled condenser (−2° C.), thermocouple-heating mantle-temperature controller assembly, overhead nitrogen inlet (0.2 liter per minute), and magnetic stirring. The magnetically stirred solution is heated to 100° C. Aniline (10.0 milliequivalents, amine to isocyanate equivalent ratio 0.3:1) is injected subsurface. Three minutes after injection of aniline the transparent solution becomes an easily stirred white slurry. The resulting reaction mixture is stirred at 100° C. for 60 minutes after the aniline is injected. The aniline concentration falls below measurable values within 10 minutes after the aniline injection. Phenyl isocyanate falls to 1.33% by weight after about 40 minutes and remains approximately at that level.

Approximately 12 grams of reaction mixture is removed for these analysis within the first 60 minutes after the aniline injection, at which time a second injection of aniline (9.74 milliequivalents) is made. The ratio of amine equivalents to isocyanate equivalents after the second aniline injection, prior to any reaction, is approximately 0.49:1. The ratio of total equivalents of aniline added in the two injections to the number of equivalents of phenyl isocyanate in the starting solution is approximately 0.6:1.

The reaction continues to be stirred at 100° C. Twenty-two minutes after the second aniline injection, the concentration of phenyl isocyanate is 0.79 weight percent and the amount of aniline is below the level of detection. The concentration of phenyl isocyanate stabilizes at about 0.70 weight percent 40-60 minutes after the second aniline addition.

EXAMPLE 12

Under a nitrogen atmosphere, a 2.01% solution (197.58 grams) of phenyl isocyanate (33.18 milliequivalents) in chlorobenzene is added to a 3 neck, 500 milliliter, round bottom, glass reactor equipped with a chilled condenser (−2° C.), thermocouple-heating mantle-temperature controller assembly, overhead nitrogen inlet (0.2 liters per minute), and magnetic stirring. The magnetically stirred solution is heated to 100° C. Aniline (5.82 milliequivalents, approximately 0.175 equivalent per equivalent of phenyl isocyanate) is injected subsurface. Nine minutes after injection of aniline the transparent solution becomes an easily stirred white slurry. A cumulative 10 minutes after the first aniline injection, a second injection of aniline (5.83 milliequivalents, approximately 0.213 equivalent per equivalent of remaining phenyl isocyanate) is made. A cumulative 20 minutes after the first aniline injection a third injection of aniline (5.79 milliequivalents, approximately 0.269 equivalent per equivalent of remaining phenyl isocyanate) is made. A cumulative 30 minutes after the first aniline injection a fourth injection of aniline (5.82 milliequivalents, about 0.370 equivalent per equivalent of remaining phenyl isocyanate) is made. The total amount of aniline added in the four injections is 0.7 equivalent per equivalent of phenyl isocyanate in the starting solution. The temperature is maintained at 100° C. with stirring throughout the process.

The phenyl isocyanate concentration is reduced to 0.53% 10 minutes after the fourth aniline injection. Aniline concentration is 0.02% at that time. By 20 minutes after the fourth aniline injection the phenyl isocyanate concentration is 0.49% and the amount of remaining aniline is below the detection limit.

EXAMPLE 13

Under a nitrogen atmosphere, a 4.50% solution (198.79 grams) of phenyl isocyanate (75.1 milliequivalents) in chlorobenzene is added to a 3 neck, 500 milliliter, round bottom, glass reactor equipped with a chilled condenser (−2° C.), thermocouple-heating mantle-temperature controller assembly, overhead nitrogen inlet (0.2 liters per minute), and magnetic stirring. The magnetically stirred solution is heated to 100° C. Aniline (4.90 grams, 52.57 milliequivalents per equivalent of phenyl isocyanate) is injected subsurface. About 10 seconds after injection of aniline the transparent solution becomes a thick, but easily stirred, white slurry. The aniline is 0.7 equivalent per equivalent of phenyl isocyanate in the starting solution. The temperature is maintained at 100° C. with stirring throughout the process. The phenyl isocyanate concentration is reduced to 1.67% 10 minutes after the aniline injection. Aniline concentration is 0.15% at that time. By 20 minutes after the aniline injection the phenyl isocyanate concentration is 1.41% and the amount of remaining aniline is 0.026%.

EXAMPLES 14-16 AND COMPARATIVE SAMPLES G AND H

Ex. 14

A solution containing 20.44 grams of a mixture of the 2,4'- and 4,4'-isomers of MDI, 406.77 grams of phenyl isocyanate and 19.906 kilograms of chlorobenzene is reacted with 234.30 grams of aniline at 157° C. under pressure for 180 minutes to a final phenyl isocyanate concentration of 0.53%. Urea compounds produced in the forgoing reaction are recovered by rotary evaporation of a portion of the product slurry and dried under vacuum (100° C./25 hours) to a constant weight. Under nitrogen, 0.0200 gram of the urea compounds are combined with 199.98 grams of a polymeric MDI (2.7 average isocyanate functionality, 134 isocyanate equivalent weight), heated with stirring to 125° C. over 14 minutes and held at that temperature for 15 minutes.

Ex. 15

Under nitrogen, 0.2000 gram of the urea compounds described in Ex. 14 are combined with 199.80 grams of the polymeric MDI described in Ex. 14, heated with stirring to 125° C. over 14 minutes and held at that temperature for 15 minutes.

Ex. 16

3.0149 grams of the product from Ex. 15 and 27.1320 grams of polymeric MDI (described in Ex. 14) are mixed together.

Comp. Sample G

For comparison, the polymeric MDI by itself (described in Ex. 14) is subjected to the same handling and heating profile. Thus, 200.00 grams of polymeric MDI are heated with stirring to 125° C. over 14 minutes and held at that temperature for 15 minutes.

Comp. Sample H

The polymeric MDI described in Ex. 14 is tested without any treatment or modification.

The isocyanate equivalent weight (IEW) of the products obtained from Examples 14-16 and Comparative Samples G and H are measured by titration. The viscosity of each are measured on a plate-and-cone rheometer at 25.6° C., with a 40 mm cone and a 54 μm gap. Molecular weights are measured on each by GPC against a 1000 MW polyethylene glycol standard, using a 1% w/v solution in anhydrous methanol. Results of the foregoing testing are as indicated in Table 17.

TABLE 17

| Sample | Ex. 14 | Ex. 15 | Ex. 16 | Comp. Sample G | Comp. Sample H |
|---|---|---|---|---|---|
| IEW | 133.74 | 133.52 | 133.69 | 133.86 | 133.82 |
| Viscosity, Pa·s | 0.206 | 0.214 | 0.200 | 0.206 | 0.197 |
| $M_w$ | 583 | 577 | 580 | 570 | 579 |
| Polydispersity | 1.33 | 1.32 | 1.33 | 1.31 | 1.33 |

As the data in Table 17 shows, the biuret-modified polymeric MDI products of Examples 14-16 have properties that are minimally changed from those of the unmodified isocyanate product. Polymeric MDI with greater amounts of biuret-modification may beneficially be diluted with fresh polymeric MDI.

What is claimed is:

1. A method for removing phenyl isocyanate from an organic solvent, comprising the steps of:
    a) contacting i) a starting solution containing at least 85 weight percent, based on the weight of the starting solution, of one or more organic solvents inert to reaction with isocyanate and amine groups and 1.5 to 15 weight percent, based on the weight of the starting solution, of phenyl isocyanate, with ii) at least one amine selected from the group consisting of aniline, MDA and PMDA, in proportions sufficient to provide 0.01 to 0.8 equivalents of primary and/or secondary amino groups per equivalent of isocyanate groups in the starting solution; and
    b) reacting at least a portion of the phenyl isocyanate with at least a portion of the amine to form a slurry of the one or more urea compounds in the one or more organic solvents.

2. The method of claim 1 wherein the starting solution and amine are combined in proportions sufficient to provide 0.2 to 0.75 equivalents of primary and/or secondary amino groups per equivalent of isocyanate groups in the starting solution.

3. The method of claim 1 wherein step a) is performed by adding the amine to the starting solution in two or more increments or continuously.

4. The method of claim 1 further comprising a step of reacting at least a portion of the one or more urea compounds with a polyisocyanate to form one or more biuret compounds.

5. The method of claim 1, further comprising recycling at least a portion of the one or more urea compounds into an MDI and/or polymeric MDI manufacturing process, which MDI and/or polymeric MDI manufacturing process comprises a step of reacting a polyamine with phosgene in solution in a process solvent to produce an MDI and/or polymeric MDI product and a step of separating the MDI and/or polymeric MDI product from the process solvent, wherein the recycling of at least a portion of the one or more urea compounds into the MDI and/or polymeric MDI manufacturing process is performed downstream of the step of reacting the polyamine with phosgene in the process solvent, and the one or more urea compounds react with a portion of the polyisocyanate product to form one or more biuret compounds during the step of separating the MDI and/or polymeric MDI product from the process solvent.

6. The method of claim 1 further comprising the step of c) separating at least a portion of the one or more organic solvents from the one or more urea compounds.

7. The method of claim 1 wherein the amine is aniline.

8. An MDI and/or polymeric MDI manufacturing process, comprising the steps of:

a) reacting aniline with formaldehyde in a solvent to produce a mixture of MDA, PMDA and unreacted aniline in the solvent;

b) distilling aniline from the mixture produced in step a) to produce a process stream containing the solvent, MDA, PMDA and residual aniline;

c) phosgenating the process stream from step b) to form an isocyanate process stream containing the solvent, MDI, one or more polymethylene polyphenylisocyanates that have at least three phenyl isocyanate groups and phenyl isocyanate;

d) separating MDI and polymethylene polyphenylisocyanates that have at least three phenyl isocyanate groups and phenyl isocyanate from the isocyanate process stream obtained in step c) by distillation to produce a solvent stream containing at least a portion of the solvent, 0.2 to 10 weight percent phenyl isocyanate based on the weight of the solvent stream and 0.0001 to 5 weight percent, based on the weight of the solvent stream, of MDI and/or one or more polymethylene polyphenylisocyanates that have at least three phenyl isocyanate groups;

e) combining the solvent stream obtained in step d) with aniline at a ratio of 0.01 to 0.8 moles of aniline per mole of phenyl isocyanate and reacting at least a portion of the aniline with phenyl isocyanate to form urea compounds;

f) recycling the urea compounds and optionally the solvent in the solvent stream into the manufacturing process downstream from step c) and into step d), whereby at least a portion of the urea compounds react during step d) with at least a portion of the MDI and/or one or more polymethylene polyphenylisocyanates that have at least three phenyl isocyanate groups to form biuret compounds.

9. The manufacturing process of claim 8 wherein step e) is performed by adding the aniline to the solvent stream obtained in step d) in two or more increments or continuously at a temperature of at least 80° C.

\* \* \* \* \*